United States Patent [19]

Nissen et al.

[11] Patent Number: 4,511,685

[45] Date of Patent: Apr. 16, 1985

[54] CHROMAN DERIVATIVES AND STABILIZED POLYPROPYLENE COMPOSITION

[75] Inventors: Axel Nissen, Leimen; Michael Horner, Neustadt; Dieter Horn, Heidelberg; Erik Lueddecke; Gernot Teege, both of Ludwigshafen, all of Fed. Rep. of Germany

[73] Assignee: BASF Aktiengesellschaft, Fed. Rep. of Germany

[21] Appl. No.: 238,593

[22] Filed: Feb. 26, 1981

[30] Foreign Application Priority Data

Mar. 19, 1980 [DE]  Fed. Rep. of Germany ....... 3010505

[51] Int. Cl.³ ..................... C08K 5/09; C07D 311/72
[52] U.S. Cl. .................... 524/110; 549/404; 549/405; 549/407
[58] Field of Search ............ 260/345.5; 549/404, 549/405, 407; 524/110

[56] References Cited

U.S. PATENT DOCUMENTS

| | | | |
|---|---|---|---|
| 3,947,473 | 3/1976 | Scott et al. | 260/345.5 |
| 4,051,153 | 9/1977 | Cohen et al. | 260/345.5 |
| 4,150,050 | 4/1979 | Cohen | 260/345.5 |

FOREIGN PATENT DOCUMENTS

| | | |
|---|---|---|
| 1114319 | 4/1962 | Fed. Rep. of Germany . |
| 1136102 | 4/1963 | Fed. Rep. of Germany . |
| 2364165 | 6/1974 | Fed. Rep. of Germany . |

*Primary Examiner*—Nicky Chan
*Attorney, Agent, or Firm*—Keil & Weinkauf

[57] ABSTRACT

Chroman derivatives of the general formula I

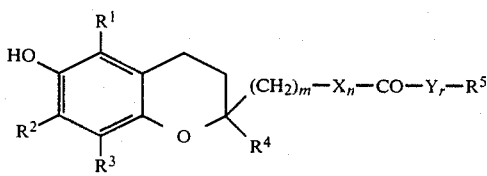

where $R^1$, $R^2$, $R^3$ and $R^4$ are each H or $C_1$–$C_4$-alkyl, $R^5$ is $C_{10}$–$C_{30}$-alkyl or $C_{10}$–$C_{30}$-alkenyl, X and Y are each O, NH or S, m is 0, 1, 2 or 3 and n and r are each 0 or 1, the preparation of compounds I by various methods known per se, and the use of the compounds as stabilizers for organic materials.

4 Claims, No Drawings

CHROMAN DERIVATIVES AND STABILIZED POLYPROPYLENE COMPOSITION

The present invention relates to novel chroman derivatives of the general formula I

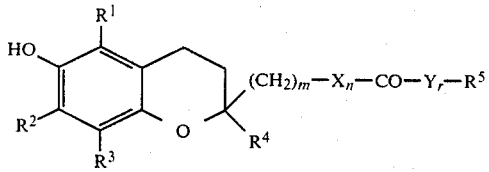

where $R^1$, $R^2$, $R^3$ and $R^4$ are each H or $C_1$-$C_4$-alkyl, $R^5$ is $C_{10}$-$C_{30}$-alkyl or $C_{10}$-$C_{30}$-alkenyl, X and Y are each O, NH or S, m is 0, 1, 2 or 3 and n and r are each 0 or 1.

The invention further relates to the preparation of the compounds I.

German Laid-Open Application DOS No. 2,364,165 discloses chroman derivatives of type I'

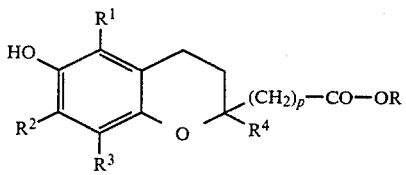

where p is 0 or 1 and R is $C_1$-$C_7$-alkyl. The novel chroman derivatives I differ from the known chroman derivatives I' essentially in possessing a $C_{10}$-$C_{30}$-alkyl group in place of the $C_1$-$C_7$-alkyl group R. Similar compounds I"

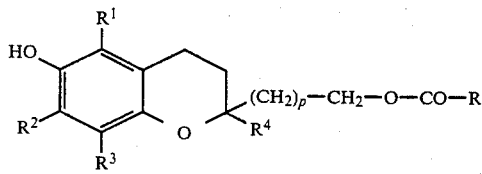

i.e. compounds which also contain a short-chain radical R, are disclosed in German Laid-Open Application DOS NO. 2,364,141.

However, compounds I' and I" are not fully satisfactory as stabilizers for plastics and other organic materials. In particular, the good stabilizing effects achieved with the structurally related compound α-tocopherol (I''', vitamin E)

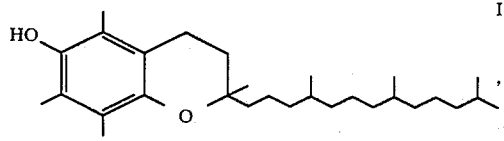

as known, for example, from German Pat. Nos. 1,114,319 and 1,136,102, are not attained.

α-Tocopherol is, however, relatively difficult to prepare and is therefore, for most purposes, too expensive to use as a stabilizer. Furthermore, α-tocopherol frequently causes undesirable discoloration. From a processing point of view, α-tocopherol, being an oily substance very prone to oxidation, also presents problems.

It is an object of the present invention to replace α-tocopherol by stabilizers which substantially have the same type of effect but are cheaper, and which produce similar or better results.

We have found that the novel chroman derivatives I defined at the outset are exceptionally suitable for use as stabilizers for organic materials, especially including plastics.

Further, we have found various processes for the preparation of the chroman derivatives I, these processes being described in more detail later. Amongst the compounds I, those where $R^1$, $R^2$, $R^3$ and $R^4$ are methyl are preferred, since chroman derivatives having this structure are particularly easy to prepare. Accordingly, the chroman radical having the structure

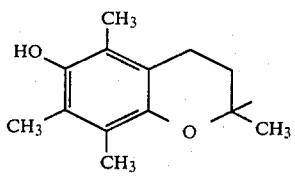

is, in the text which follows, referred to as radical A, so that the compounds I can also, for brevity, be written as $$A-(CH_2)_m-X_n-CO-Y_r-R^5 \quad \text{I.}$$

If $R^1$, $R^2$, $R^3$ or $R^4$ are other than methyl, this is indicated by a note such as "A($R^4$=H)", which, in the example chosen, means that $R^1$, $R^2$ and $R^3$ are methyl and $R^4$ is hydrogen.

Compounds I where $R^1$, $R^2$, $R^3$ and $R^4$ are other than methyl can be obtained in a similar manner to the compounds containing group A, and, according to our observations to date, their effect as stabilizers is about the same as that of the tetramethylchroman derivatives.

An essential structure for achieving the stabilizing effect is the alkyl or alkenyl radical $R^5$ which, in accordance with the definition given, should be of 10 to 30 carbon atoms, linear radicals and radicals with methyl branches being preferred. The nature of the group $-X_n-CO-Y_r-$ is of lesser importance from the point of view of the stabilizing properties of I, since the function of this group is primarily to link the radical $R^5$ to the chroman group. The number of methyl groups, m, also has no discernible influence on the stabilizing properties. The other properties, inter alia the compatibility and miscibility with the substrate, can however depend on m and on the group $-X_n-CO-Y_4-$. For example, compounds I, where X and/or Y are —NH—, are preferred for stabilizing nylons, because of the processing technique involved, whilst for hydrophobic plastics, such as polypropylene, compounds I having an ester structure (X or Y=O) are advantageous.

The following 16 types of compounds, Ia-Ip, correspond to the different types of group $-X_n-CO-Y_4-$:

| | | |
|---|---|---|
| Ia | n = r = o | —CO— |
| Ib | n = O, Y = O | —CO—O— |
| Ic | n = O, Y = NH | —CO—NH— |
| Id | n = O, Y = S | —CO—S— |
| Ie | X = O, r = O | —O—CO— |
| If | X = O, Y = O | —O—CO—O— |

| | | |
|---|---|---|
| Ig | X = O, Y = NH | —O—CO—NH— |
| Ih | X = O, Y = S | —O—CO—S— |
| Ii | X = NH, r = O | —NH—CO— |
| Ij | X = NH, Y = O | —NH—CO—O— |
| Ik | X = NH, Y = NH | —NH—CO—NH— |
| Il | X = NH, Y = S | —NH—CO—S— |
| Im | X = S, r = O | —S—CO— |
| In | X = S, Y = O | —S—CO—O— |
| Io | X = S, Y = NH | —S—CO—NH— |
| Ip | X = S, Y = S | —S—CO—S— |

The general principle of preparation of these compounds is to react a chroman derivative of type

A—(CH$_2$)$_m$—CO—Y—H or A—(CH$_2$)$_m$—XH with a compound R$^5$—OH or R$^5$—Y$_2$—CO—OH or a functional derivative thereof, such as a chloride or methyl ester.

It is also possible to start from a chroman intermediate of the type

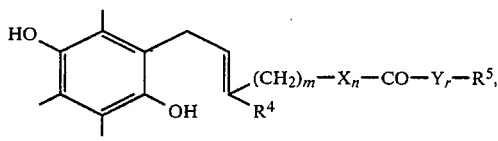

prepare the quinone from this compound, cyclize this, and hydrogenate the resulting chrom-2-ene. The linkage of the chroman moiety of the molecule to the radical R$^5$ via the —X$_n$—CO—Y$_r$— group is effected in a similar manner to that described in a general form above.

In all these syntheses it may furthermore be advisable to protect the 6-OH group in a conventional manner by means of a radical which can easily be eliminated again, for example benzyl, and then to eliminate this radical in the last step of the synthesis.

More specifically, the compounds Ia–Ip may be obtained by the following methods (a)–(p):

(a) Preparation of the ketones Ia

An acid halide IIa

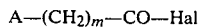

A—(CH$_2$)$_m$—CO—Hal       IIa in which the 6-OH group is protected by a protective group, preferably by a benzyl, is used as the starting material and is reacted in a conventional manner with a Grignard compound R$^5$-MgHal in the presence of CdCl$_2$. The adduct is then hydrolyzed, with elimination of the protective group. Working up, to give compound Ia, is then carried out in a conventional manner.

It is also possible to eliminate the protective group hydrogenolytically after the hydrolysis.

The acid halides IIa are known from German Laid-Open Application DOS No. 2,364,141 or are obtainable by the method described therein.

(b) Preparation of the esters Ib (b$_1$) Esterification processes

The esters Ib are particularly easily obtainable by conventional acid-catalyzed esterification of the carboxylic acids IIb

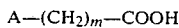

A—(CH$_2$)$_m$—COOH       IIb with alcohols R$^5$—OH (IIIb). The starting compounds IIb are known, for example from German Laid-Open Application DOS No. 2,364,141.

Esterification is a generally known reaction, with numerous embodiments in respect of the acid used, the removal of the water of reaction, and the temperature and reaction time employed, so that further discussion is superfluous. It should merely be mentioned that in most cases it is advisable to employ the acid IIb in excess. The unconsumed acid can then be separated from the ester Ib by means of aqueous alkali, after which it can easily be recovered by acidifying the aqueous alkaline solution. If purification of Ib is necessary at all, it can be effected by recrystallization, a suitable medium, in most cases, being a methanol/water mixture. Instead of using the alcohols R$^5$—OH, the halides R$^5$-Hal or the esters with inorganic or organic acids may be employed. In that case, the esterification or trans-esterification is carried out in the presence of a weak base and, advantageously, of a solvent. This method also is generally known so that further discussion is superfluous. Conversely, it is possible to start from a halide or ester of IIb and react this with the alcohol IIIb to give the ester Ib.

A further possible method of preparation of the ester Ib is to react the easily obtainable nitrile IIb'

A—(CH$_2$)$_m$—Cn       IIb' with an alcohol in the presence of an inorganic acid. The preparation of the nitriles IIb' is described in our earlier German Patent Application No. P 29 09 601.

(b$_2$) Cyclization process

In respect of the total synthesis starting from trimethylhydroquinone (or its homologs) it can be advantageous first to prepare an open-chain trimethylhydroquinone derivative, which contains the group —(CH$_2$)$_m$—CO—O—R$^5$, and to effect the cyclization to the chroman at the end. This method of synthesis can be illustrated as follows:

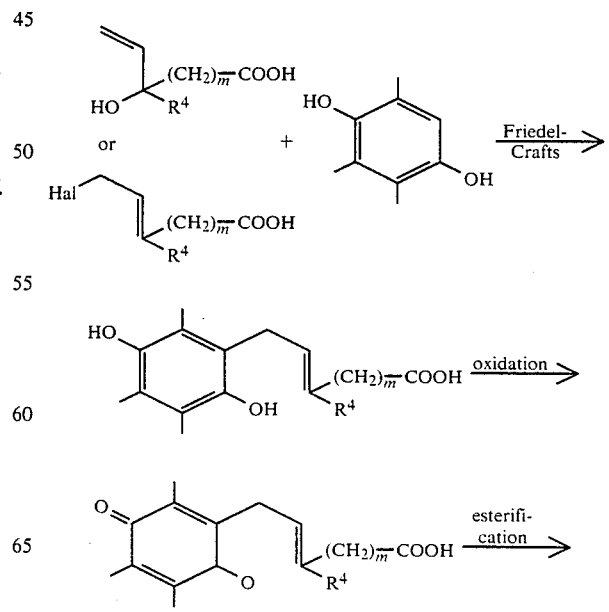

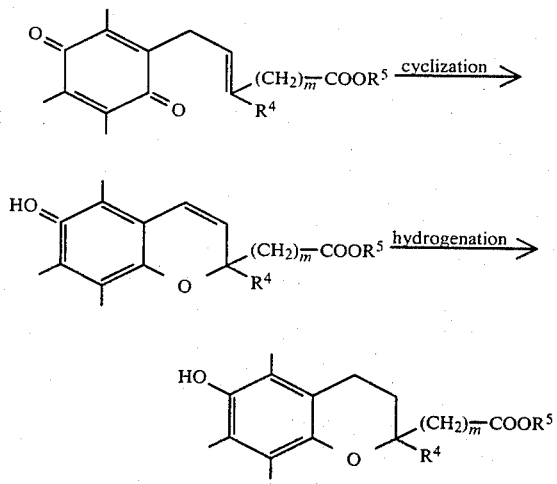

The esterification step, which may be carried out by a method described under (b₁), can, in this scheme, also be carried out at an earlier stage. The reaction of the trimethylhydroquinone with the alkyl compound is carried out in a conventional manner, by one of the Friedel-Crafts synthesis methods. The oxidation of the intermediate formed, to give the quinone, takes place easily and can be effected with, for example, air. The oxidation is as a rule necessary because only the quinone can be cyclized to the chroman six-membered ring; cyclizing the hydroquinone would in most cases give an O-containing five-membered ring. The cyclization is also carried out in a conventional manner, for example by means of a tertiary nitrogen base, eg. triethylamine or pyridine.

The subsequent hydrogenation of the chroman derivative formed can also be carried out by conventional methods.

(c) Preparation of the amides Ic

This is carried out by reacting a carboxylic acid IIb or a functional derivative thereof, such as a halide or ester, with an amine $R^5$—$NH_2$, by a conventional method.

(d) Preparation of the thioesters Id

The preparation of the thioesters Id is carried out similarly to the esterification Ib, but starting from a thiol $R^5$—SH instead of an alcohol $R^5$—OH.

(e) Preparation of the esters Ie

For this, a chroman derivative IIe

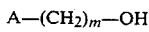
A—(CH$_2$)$_m$—OH    IIe obtained, for example, by Friedel-Crafts adduct formation of a diol

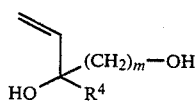

with trimethylhydroquinone, is used as the starting compound.

The esterification of IIe to give Ie is carried out in a conventional manner, with an acid $R^5$—COOH (IIIe) or a functional derivative thereof.

(f) Preparation of the carbonates If

A compound IIe is reacted, similarly to method (e), with a chloroformic acid ester $R^5$—O—CO—Hal (IIIf) or a carbonate, eg. $R^5$—O—CO—O—CH$_3$.

(g) Preparation of the urethanes Ig

The simplest method for the preparation of these compounds is adduct formation of an isocyanate $R^5$—N=C=O (IIIg) with an alcohol IIe, though it is advisable to protect the 6-OH group of the chroman.

Instead of the isocyanate IIIg, a corresponding carbamyl halide $R^5$—NH—CO—Hal, or a urethane, eg. $R^5$—NH—CO—O—CH$_3$, may be employed.

(h) Preparation of the monothiocarbonates Ih

These compounds are obtained by method (f), except that the corresponding thio derivatives (IIIh), ie. $R^5$—S—CO—Hal or $R^5$—S—CO—O—CH$_3$ are employed.

(i) Preparation of the amides Ii

The starting compounds are the amines IIi

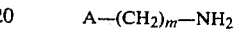
A—(CH$_2$)$_m$—NH$_2$    IIi which may be prepared in a conventional manner by hydrolysis of nitriles IIb'.

The amines IIi are then converted to the amides Ii in a conventional manner, by means of a carboxylic acid IIIe or a functional derivative thereof.

(j) Preparation of the urethanes Ij

The urethanes Ij may be obtained by a method similar to (f), from an amine IIi and a chloroformic acid ester IIIf or carbonate $R^5$—O—CO—O—CH$_3$.

(k) Preparation of the ureas Ik

These compounds are obtained by reacting an amine IIi in a conventional manner, by one of methods (g), with an isocyanate (IIIg) or with a corresponding carbamyl halide or urethane.

(l) Preparation of the thiocarbamates Il

An amine IIi is reacted, by method (h), with a thio compound IIIh, $R^5$—S—CO—Hal or $R^5$—S—CO—O—CH$_3$.

(m)–(p) Preparation of the thio compounds Im–Ip

These compounds are prepared similarly to methods (e)–(h), by starting from the corresponding thiol IIm

A—(CH$_2$)$_m$—SH    IIm which in turn may be obtained by a method described for the alcohol IIe, but using the corresponding sulfur-containing starting compound.

The novel chroman derivatives I are outstandingly useful as heat stabilizers, light stabilizers and oxidation stabilizers for organic materials. Examples of relevant organic materials are fats, oils, waxes, pharmaceutical and cosmetic formulations and especially plastics. Depending on the severity of the conditions to which the plastics are exposed, the stabilizers are used in concentrations of from 0.01 to 1.0, as a rule from 0.1 to 0.5, % by weight, based on the amount of plastic. For highly sensitive substrates, for example vitamins, the concentrations can be as high as 20% by weight. The novel stabilizers may be used alone or mixed with other stabilizers, especially with synergistic agents. The latter are compounds which alone have little or no stabilizing effect but, when used conjointly with stabilizers, markedly improve their effect. Examples of such synergistic agents are calcium stearate and distearyl thiodipropionate

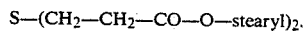
S—(CH$_2$—CH$_2$—CO—O—stearyl)$_2$.

The synergistic agent is in general employed in an amount of from 50 to 500% by weight, based on the amount of stabilizer.

In general, stabilizers serve to protect the organic materials from changes and decomposition, which in the case of plastics means, in the main, against degradation and undesirable crosslinking of the macromolecules, these being changes which manifest themselves as aging, embrittlement, discoloration and lowering of softening point.

The following criteria are particularly relevant in assessing the suitability and effectiveness of stabilizers:

1. Color

The stabilizer should not discolor the substrate. This requirement, which is of course particularly important for colorless plastics, is satisfactorily or excellently met by the novel stabilizers in the case of most plastics; as a rule, the novel compounds are superior to conventional stabilizers, including α-tocopherol. The quantitative determination of the color characteristics can be carried out by various methods, for example by the yellowness test—ASTMD 1925.

2. Processing stability

This refers to the degree to which the properties of thermoplastics remain constant when exposed to mechanical stresses and heat during molding processes, such as extrusion and injection-molding. In this respect, the novel stabilizers give particularly good results. A measure of the processing stability is the change in melt characteristics of the thermoplastic after repeated molding and remelting. The corresponding melt index test is described in DIN 53,735. Another important criterion of processing stability is constancy of color, which can be assessed by, for example, the yellowness test.

3. Long-term stability

The behavior of plastics when exposed to severe thermal and oxidative conditions is an indication of the period for which the quality of the plastic will remain constant when the material is used for a particular application; this means that the data determined by the corresponding test (DIN 53,383, page 1) permit an estimate of the useful life of the plastic article. The novel stabilizers offer advantages in long-term stability when used in conjunction with synergistic agents.

Further details concerning tests of the quality of the novel stabilizers are to be found in the experiments on the effects of the stabilizers.

EXAMPLES OF THE PREPARATION OF THE CHROMAN DERIVATIVES I

Examples 1 to 14

Preparation of chroman derivatives
A-$(CH_2)_m$—CO—O—$R^5$ (Ib) by method (b)

In each of Examples 1 to 12, 80 g (0.32 mole) of 6-hydroxy-2,5,7,8-tetramethylchroman-2-carboxylic acid A—$(CH_2)_n$—COOH were refluxed with 0.28 mole of an alcohol $R^5$—OH in a solution of 500 ml of toluene and 10 g of phosphoric acid until no further water was eliminated. 400 ml of aqueous $NaHCO_3$ solution were then used to remove the excess acid from the organic phase, and the latter was worked up in a conventional manner. Thereafter, the crude ester Ib was recrystallized from methanol/water.

In each of Examples 13 and 14, 10 g (43 millimoles) of the nitrile A-CN were dissolved in 50 ml of anhydrous tetrahydrofuran and 30 g of the alcohol $R^5$—OH, the solution was saturated with hydrogen chloride at 0° C. and kept at this temperature for 3 days, and the reaction mixture was worked up in a conventional manner.

The results are summarized in Table 1. Where one of the substituents $R^1$-$R^4$ of the radical A is not methyl, this fact is noted by indicating the actual substituent present in place of methyl.

TABLE 1

| | Compounds A—COO—$R^5$ (Ib) | | | | |
|---|---|---|---|---|---|
| Example No. | | | | Ester Ib | |
| Compound No. | Difference from A | m | $R^5$ | M.p., °C. | Yield % |
| 1 | — | 0 | n-Dodecyl | 50 | 90 |
| 2 | — | 0 | 3,7-Dimethyloct-7-en-1-yl | 53–55 | 88 |
| 3 | — | 0 | n-Tetradecyl | 62–63 | 93 |
| 4 | — | 0 | n-Hexadecyl | 66–68 | 91 |
| 5 | — | 0 | n-Octadecyl | 67–69 | 94 |
| 6 | — | 0 | n-Eicosyl | 58–60 | 90 |
| 7 | — | 0 | n-Octadec-9-enyl | 35–37 | 89 |
| 8 | — | 0 | 3,7,11,15-Tetramethylhexadecyl | oil | 93 |
| 9 | $R^3$ = H | 0 | n-Dodecyl | 57–59 | 90 |
| 10 | $R^4$ = iso-Propyl | 0 | n-Dodecyl | 49–51 | 41 |
| 11 | — | 1 | n-Dodecyl | 40–43 | 85 |
| 12 | — | 1 | n-Octadecyl | 40–42 | 88 |
| 13 | — | 0 | 3,7-Dimethyloctyl | 48–49 | 81 |
| 14 | — | 0 | 3,7,11,15-Tetramethylhexadecyl | oil | 80 |

Examples 15 to 23

Preparation of esters A—$(CH_2)_m$—O—CO—$R^5$ (Ie)

In each of Examples 15 to 21, 30 g (0.12 mole) of the chroman derivative A—$(CH_2)_m$—OH and the equimolar amount of a carboxylic acid $R^5$—COOH were refluxed in 1 liter of toluene, in the presence of 3 g of p-toluenesulfonic acid, until no further water was eliminated. The mixture was then worked up in a conventional manner. The crude esters Ie were purified by recrystallization from methanol/water.

In Examples 22 and 23, the corresponding acid chlorides were employed instead of the acids $R^5$—COOH, and the esterification was carried out in the presence of an equimolar amount of pyridine.

The results are shown in Table 2.

TABLE 2

| Compounds A—$(CH_2)_m$—O—CO—$R^5$ (Ie) | | | | |
|---|---|---|---|---|
| Example No. | | | Ester Ie | |
| Compound No. | m | $R^5$—COOH | M.p., °C. | Yield % |
| 15 | 2 | Stearic acid | 52 | 94 |
| 16 | 2 | Palmitic acid | 52–54 | 93 |
| 17 | 2 | Oleic acid | Oil | 95 |
| 18 | 2 | Lauric acid | 53–54 | 92 |
| 19 | 2 | Linoleic acid | Oil | 88 |
| 20 | 2 | Linolenic acid | Oil | 88 |
| 21 | 2 | Coconut fatty acid | Oil | 92 |
| 22 | 1 | Stearoyl chloride | 44 | 81 |
| 23 | 1 | Lauroyl chloride | 42 | 83 |

Examples 24 and 25

Preparation of carbonates
A—(CH$_2$)$_m$—O—CO—O—R$^5$ (If)

The chroman derivative A—(CH$_2$)$_m$—OH was reacted with a chloroformic acid ester R$^5$—O—CO—Cl by a method similar to Examples 22 and 23. The results are shown in Table 3.

TABLE 3

| Example No. Compound No. | m | R$^5$ | Carbonate If M.p., °C. | Yield % |
|---|---|---|---|---|
| 24 | 2 | n-Hexadecyl | 60 | 91 |
| 25 | 1 | n-Hexadecyl | 48–50 | 73 |

Example 26

Preparation of an amide A—CH$_2$—NH—CO—R$^5$ (Ic)

4.7 g (0.02 mole) of the aminomethylchroman derivative A—CH$_2$—NH$_2$ in 150 ml of toluene were reacted with 5.5 g (0.02 mole) of palmitoyl chloride in the presence of 3 g of piperidine. Conventional working up gave the compound A—CH$_2$—NH—CO-palmityl in 88% yield.

Example 27

Preparation of a urethane
A—CH$_2$—NH—CO—O—R$^5$ (Ij)

Using a method similar to Example 26, the aminomethylchroman derivative was reacted with 6.13 g (0.02 mole) of n-hexadecyl chloroformate. Conventional working up gave a 90% yield of the urethane A—CH$_2$—NH—CO—O-n-hexadecyl as a colorless oil.

Example 28

Preparation of an amide A—CH$_2$—NH—CO—R$^5$ (Ic) via an OH-protected chroman derivative 10 g (31 millimoles) of 6—benzyl—A—CH$_2$—NH$_2$, prepared by reaction of A—CH$_2$—NH$_2$ with benzyl chloride in the presence of potassium carbonate and dimethylformamide (melting point of the hydrochloride 155° C.) were reacted, by a method similar to Example 26, with palmitoyl chloride, and the reaction mixture was worked up in a conventional manner to give 6-benzyl—A—CH$_2$—NH—CO-n-pentadecyl. The yield of this compound was 98%; melting point 83°–84° C. The benzyl group was then eliminated by hydrogenation at 55° under 10 bar hydrogen pressure in the presence of a Pd/charcoal catalyst. Working up gave the free A—CH$_2$—NH—CO-n-pentadecyl as a yellowish oil, in 87% yield.

Example 29

Preparation of the compound (1) by method (b$_2$)

3 liters of hydrogen chloride were passed into a mixture of 9 g (0.06 mole) of trimethylhydroquinone, 8 g (0.06 mole) of 4-chloro-2-methylcrotonic acid, 3 g of anhydrous zinc chloride and 80 ml of heptane in the course of one hour at 98° C. After heating for a further two hours, the heptane phase was decanted, the oily residue was mixed with 50 ml of methanol and the mixture was stirred for 24 hours at 20° C. This resulted in a precipitate, which was separated off. Water was added to the methanolic mother liquor, whereupon a further precipitate formed. The two precipitates were combined and recrystallized from water. The yield of 4-(2,5-dihydroxy-3,4,6-trimethylphenyl)-2-methylcrotonic acid was 62%; melting point 208° C. (with decomposition).

This compound was esterified with n-dodecanol by the method of Examples 1 to 12. The yield of ester was 79%, based on the acid; melting point 40°–43° C. The ester and 0.1 g of copper(I)-bis-pyridine chloride were dissolved in 250 ml of methanol, and air was passed through this solution. This converted the hydroquinone to the corresponding quinone (a yellow oil); yield: quantitative.

12 g of the quinone derivative in 20 ml of anhydrous pyridine were refluxed for 1.5 hours, resulting in the chromene derivative

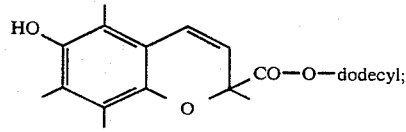

yield 73%, based on quinone; melting point 48°–51° C.

The chroman derivative (1) was hydrogenated at 50° C. and 10 bar hydrogen pressure over a Pd/charcoal catalyst. The yield was 96%, based on chromene.

Experiments on the stabilizing action of the chroman derivatives I

1. Color of polypropylene

The color quality was measured in terms of the Yellowness Index (YI), by the yellowness test (ASTMD 1925).

The test material used was additive-free dechlorinated polypropylene; in each case the stabilizer was incorporated into the polypropylene in the same manner, and the material was then converted into 15-mm granules or sheets of 1 mm thickness. The YI values quoted are each the mean of two measurements. The higher the values, the lower the color quality. The results are shown in Table 4. The values roughly correspond to the following (visually) perceptible discolorations of the test material:

2 no discernible discoloration
3–5 very slight discoloration
5–10 slight but distinctly discernible discoloration
10–20 marked discoloration
20 severe discoloration

TABLE 4

| | Yellowness Index YI of polypropylene sheets and granules | | | |
|---|---|---|---|---|
| Experiment No. | Stabilizer* | From Example | Amount % by weight | YI Index Sheets | Granules |
| Comparison | | | | | |
| 1 | no stabilizer | — | 0.1 | 0 | 1 |
| 2 | Q** | — | 0.1 | 1 | 8 |
| 3 | α-tocopherol | — | 0.1 | 9 | 28 |

TABLE 4-continued

Yellowness Index YI of polypropylene sheets and granules

| Experiment No. | Stabilizer* | From Example | Amount % by weight | YI Index Sheets | YI Index Granules |
|---|---|---|---|---|---|
| 4 | —CO—O—CH$_3$ | — | 0.1 | 12 | 36 |
| 5 | —CO—O—n-heptyl | — | 0.1 | 7 | 25 |
| 6 | —CH$_2$—CO—O—CH$_3$ | — | 0.1 | 9 | 34 |
| 7 | Q | — | 0.1 | 2 | 4 |
|  | + calcium stearate | — | 0.2 |  |  |
| 8 | α-tocopherol | — | 0.1 | 4 | 15 |
|  | calcium stearate | — | 0.2 |  |  |
|  | DSDP*** | — | 0.2 |  |  |
| 9 | —CH$_2$—CO—O—CH$_3$ | — | 0.1 | 5 | 17 |
|  | Ca stearate | — | 0.2 |  |  |
|  | DSDP | — | 0.2 |  |  |
| According to the invention |  |  |  |  |  |
| 10 | —CO—O—3,7-dimethyl-octyl | 2 | 0.1 | 6 | 23 |
| 11 | —CO—O—n-dodecyl | 1 | 0.1 | 5 | 22 |
| 12 | —CO—O—3,7,11,15-tetramethylhexadecyl | 8 | 0.1 | 4 | 20 |
| 13 | —CH$_2$—CO—O—n-dodecyl | 11 | 0.1 | 9 | 30 |
| 14 | —CH$_2$—CO—O—n-octadecyl | 12 | 0.1 | 20 | 30 |
| 15 | —CO—O—oleyl | 7 | 0.1 | 7 | 23 |
| 16 | —CO—O—n-eicosyl | 6 | 0.1 | 4 | 17 |
| 17 | —CH$_2$—CH$_2$—O—CO—O—hexadecyl | 24 | 0.1 | 5 | 23 |
| 18 | —CH$_2$—NH—CO—n-pentadecyl | 26 | 0.1 | 4 | 22 |
| 19 | —CH$_2$—O—CO—n-heptadecyl | 22 | 0.1 | 5 | 23 |
| 20 | —CH$_2$—CH$_2$—O—CO—n-pentadecyl | 16 | 0.1 | 6 | 22 |
| 21 | —CH$_2$—CH$_2$—O—CO—n-heptadecyl | 15 | 0.1 | 5 | 22 |
| 22 | —CO—O—n-dodecyl | 1 | 0.1 | 2 | 8 |
|  | Ca stearate |  | 0.2 |  |  |
|  | DSDP |  | 0.2 |  |  |
| 23 | —CO—O—3,7,11,15-tetramethylhexadecyl | 8 | 0.1 | 2 | 9 |
|  | Ca stearate |  | 0.2 |  |  |
|  | DSDP |  | 0.2 |  |  |
| 24 | —CH$_2$—CO—O—n-dodecyl | 11 | 0.1 | 6 | 18 |
|  | Ca stearate |  | 0.2 |  |  |
|  | DSDP |  | 0.2 |  |  |
| 25 | —CH$_2$—CH$_2$—O—CO—n-heptadecyl | 15 | 0.1 | 3 | 10 |
|  | Ca stearate |  | 0.2 |  |  |
|  | DSDP |  | 0.2 |  |  |

*identified by the radical —(CH$_2$)$_m$—X$_n$—CO—Y$_r$—R$^5$ in the compound A—(CH$_2$)$_m$—X$_n$—CO—Y$_r$—R$^5$, unless stated otherwise
**neopentyl glycol tetra-[3-(3,5-di-tert.-butyl-4-hydroxyphenyl)-propionate] (a commercial product)
***distearyl thiodipropionate 2. Processing stability of polypropylene The polypropylene samples (the material used being the same as for the color test) were subjected to six extrusion and granulation sequences. The quotient MFI$_6$/MFI$_1$ was calculated from the melt indices (MFI) (for method of determination, see DIN 53,735) after the first and sixth extrusions. The higher this quotient, the lower the processing stability. The color measurements correspond to that in the color test. The results are shown in Table 5.

TABLE 5

Melt index quotient MFI$_6$/MFI$_1$ and yellowness index of polypropylene

| Experiment No. | Stabilizer$^{(x)}$ | From Example | Amount, % by weight | MFI$_6$/MFI$_1$ | YI$_1$ | YI$_6$ | Δ |
|---|---|---|---|---|---|---|---|
| Comparison |  |  |  |  |  |  |  |
| 26 | without stabilizer | — | — | 7.3 | 1 | 5 | 4 |
| 27 | Q$^{(xx)}$ | — | 0.1 | 2.5 | 7 | 20 | 13 |
| 28 | α-tocopherol | — | 0.1 | 2.1 | 28 | 38 | 10 |
| 29 | —CO—O—CH$_3$ | — | 0.1 | 1.9 | 36 | 46 | 10 |
| 30 | —CO—O—n-heptyl | — | 0.1 | 1.9 | 25 | 32 | 7 |
| 31 | —CH$_2$—CO—O—CH$_3$ | — | 0.1 | 2.2 | 34 | 44 | 10 |
| 32 | Q |  | 0.1 |  |  |  |  |
|  | Ca stearate |  | 0.2 | 2.9 |  |  |  |
| 33 | α-tocopherol | — | 0.1 |  |  |  |  |

TABLE 5-continued

Melt index quotient MFI$_6$/MFI$_1$ and yellowness index of polypropylene

| Experiment No. | Stabilizer[x] | From Example | Amount, % by weight | MFI$_6$/MFI$_1$ | YI$_1$ | YI$_6$ | Δ |
|---|---|---|---|---|---|---|---|
| | DSDP[xxx] | — | 0.2 | | | | |
| | Ca stearate | — | 0.2 | 1.5 | 15 | 20 | 5 |
| According to the invention | | | | | | | |
| 34 | —CO—O—3,7-dimethyloctyl | 2 | 0.1 | 1.9 | 23 | 32 | 9 |
| 35 | —CO—O—n-dodecyl | 1 | 0.1 | 1.6 | 22 | 31 | 9 |
| 36 | —CO—O—n-tetradecyl | 3 | 0.1 | 1.6 | 18 | 33 | 15 |
| 37 | —CO—O—n-hexadecyl | 4 | 0.1 | 1.6 | 22 | 32 | 10 |
| 38 | —CO—O—n-octadecyl | 5 | 0.1 | 1.6 | 18 | 32 | 14 |
| 39 | —CO—O—n-eicosyl | 6 | 0.1 | 1.6 | 18 | 31 | 13 |
| 40 | —CO—O—oleyl | 7 | 0.1 | 1.6 | 23 | 40 | 17 |
| 41 | —CO—O—3,7,11,15-tetramethylhexadecyl | 8 | 0.1 | 1.6 | 20 | 28 | 8 |
| 42 | —CH$_2$—CO—n-dodecyl | 11 | 0.1 | 1.9 | 30 | 38 | 8 |
| 43 | —CH$_2$—CO—n-octadecyl | 12 | 0.1 | 1.7 | | | | |
| 44 | —CH$_2$—CH$_2$—O—CO—O—n-hexadecyl | 24 | 0.1 | 1.6 | | | | |
| 45 | —CH$_2$—O—CO—n-heptadecyl | 22 | 0.1 | 1.6 | 24 | 37 | 13 |
| 46 | —CH$_2$—CH$_2$—O—CO—n-heptadecyl | 15 | 0.1 | 1.6 | 22 | 36 | 14 |
| 47 | —CO—O—n-dodecyl | 1 | 0.1 | | | | | |
| | Ca stearate | | 0.2 | | | | |
| | DSDP | | 0.2 | 1.7 | 8 | 26 | 18 |
| 48 | —CO—O—3,7,11,15-tetramethylhexadecyl | 8 | 0.1 | | | | |
| | Ca stearate | | 0.2 | | | | |
| | DSDP | | 0.2 | 1.7 | 9 | 26 | 17 |
| 49 | —CH$_2$—CO—O—n-dodecyl | 11 | 0.1 | | | | |
| | Ca stearate | | 0.2 | | | | |
| | DSDP | | 0.2 | 1.7 | 19 | 37 | 16 |
| 50 | —CH$_2$—CH$_2$—O—CO—n-heptadecyl | 15 | 0.1 | | | | |
| | Ca stearate | | 0.2 | | | | |
| | DSDP | | 0.2 | 1.7 | 10 | 24 | 14 |

[x], [xx] and [xxx]Cf. footnotes to Table 4

3. Long-term stability of polypropylene
3.1 Oven aging

Polypropylene sheets as specified in the color test were subjected to oven aging, as described in DIN 53,383, page 1, by heating the sheets in an oven, with access of fresh air, at 140° C. until they showed noticeable embrittlement. The visual test was carried out every 24 hours, ie. the aging time was measured in days. The lower the values, the lower the long-term stability. The values are mean values of 10 measurements and each have a deviation of up to about 5%. The results are summarized in Table 6.

3.2 Oxygen absorption at 180° C.

Polypropylene samples were heated in the molten state at 180° C. under pure oxygen until a significant consumption of oxygen commenced. This induction time was recorded in minutes. The results are shown in Table 7.

TABLE 6

Oven aging of polypropylene at 140° C.

| Experiment No. | Stabilizer[x] | From Example No. | Amount, % by weight | Aging time (days) |
|---|---|---|---|---|
| Comparison | | | | |
| 51 | without stabilizer | — | — | 1 |
| 52 | Q[xx] | — | 0.1 | 40 |
| 53 | α-tocopherol | — | 0.1 | 3 |
| 54 | —CO—O—CH$_3$ | — | 0.1 | 1 |
| 55 | —CO—O—n-heptyl | — | 0.1 | 1 |
| 56 | —CH$_2$—CO—O—methyl | — | 0.1 | 1 |
| 57 | Q | — | 0.1 | 31 |
| | Ca stearate | — | 0.2 | |
| 58 | α-tocopherol | — | 0.1 | 14 |
| | Ca stearate | — | 0.2 | |
| | DSDP[xxx] | — | 0.2 | |
| According to the invention | | | | |
| 59 | —CO—O—3,7-dimethyloctyl | 2 | 0.1 | 1 |
| 60 | —CO—O—n-dodecyl | 1 | 0.1 | 3 |
| 61 | —CO—O—n-tetradecyl | 3 | 0.1 | 3 |
| 62 | —CO—O—n-hexadecyl | 4 | 0.1 | 3 |
| 63 | —CO—O—n-octadecyl | 5 | 0.1 | 3 |
| 64 | —CO—O—n-eicosyl | 6 | 0.1 | 3 |
| 65 | —CO—O—n-oleyl | 7 | 0.1 | 3 |
| 66 | —CO—O—3,7,11,15-tetramethylhexadecyl | 8 | 0.1 | 3 |
| 67 | —CH$_2$—CO—O—n-dodecyl | 11 | 0.1 | 1 |
| 68 | —CH$_2$—CO—O—n-octadecyl | 12 | 0.1 | 1 |
| 69 | —CH$_2$—O—CO—n-heptadecyl | 22 | 0.1 | 3 |
| 70 | —CH$_2$—CH$_2$—O—CO—heptadecyl | 15 | 0.1 | 3 |
| 71 | —CH$_2$—CH$_2$—O—CO—O—n-hexadecyl | 24 | 0.1 | 3 |
| 72 | —CO—NH—n-dodecyl | — | 0.1 | 3 |
| 73 | —CO—S—n-dodecyl | — | 0.1 | 3 |
| 74 | —CH$_2$—NH—CO—n-pentadecyl | — | 0.1 | 3 |
| 75 | —CO—O—3,7,11,15-tetramethylhexadecyl | 8 | 0.1 | 18 |
| | Ca stearate | — | 0.2 | |
| | DSDP | — | 0.2 | |
| 76 | —CH$_2$—CO—O—n-dodecyl | 11 | 0.1 | 17 |
| | Ca stearate | — | 0.2 | |
| | DSDP | — | 0.2 | |
| 77 | —CH$_2$—CH$_2$—O—CO—n-heptadecyl | 15 | 0.1 | 19 |
| | Ca stearate | — | 0.2 | |
| | DSDP | — | 0.2 | |

[x], [xx] and [xxx]Cf. footnotes to Table 4

TABLE 7

Oxygen absorption of polypropylene melts at 180° C.

| Experiment No. | Stabilizer* | From Example | Amounts % by weight | Induction time (min) |
|---|---|---|---|---|
| Comparison | | | | |
| 78 | without stabilizer | — | — | 6 |
| 79 | Q** | — | 0.1 | 77 |
| 80 | —CO—O—CH$_3$ | — | 0.1 | 98 |
| 81 | —CO—O—n-heptyl | — | 0.1 | 55 |
| According to the invention | | | | |
| 82 | —CO—O—3,7-dimethyloctyl | 2 | 0.1 | 63 |
| 83 | —CO—O—n-dodecyl | 1 | 0.1 | 79 |
| 84 | —CO—O—n-eicosyl | 6 | 0.1 | 76 |
| 85 | —CH$_2$—CH$_2$—O—CO—n-heptadecyl | 15 | 0.1 | 73 |

*and **Cf. footnotes to Table 4

4. Stability of β-carotin

4.1 Light stability 10 mg portions of a dry powder which consisted of 88.5 percent by weight of polyvinylpyrrolidone, 10% by weight of β-carotin and 1.5% by weight of a stabilizer were dissolved in 10 ml of air-saturated water. The intense yellow color of the clear solution corresponded to a light absorption maximum of 430 nm. At this wavelength, the extinction of a 1 cm layer of the solution was 0.8, and this was taken, for reference purposes, as 100%.

To determine the stability of the β-carotin to light, the solution was exposed to monochromatic ultraviolet light from a mercury high-pressure lamp (365 nm; 1 mW/cm$^2$). The decoloration of the solution, ie. the decrease in extinction, is a measure of the destruction of the β-carotin, by the above irradiation. Table 8 shows the time in minutes required for the extinction to fall to 1/e-th, ie. to about 0.4. For further details of this method of determination cf. J. Photochem., 7 (1977), 355.

4.2 Shelf life

The β-carotin dry powder of the above composition was stored for 7 days in the dark at 25° C. The extinction in percent of the original values E$_o$ (=100%) was then determined. Solutions of 50 mg of the dry powder in 100 ml of chloroform were used for the measurements. The results of this test are also shown in Table 8.

TABLE 8

Light stability and shelf life of β-carotin (stabilizer concentration 15% by weight, based on carotin)

| Experiment No. | Stabilizer$^{(x)}$ | From Example | Light stability min. | Shelf life % of E after 7 days |
|---|---|---|---|---|
| Comparison | | | | |
| 86 | without stabilizer | — | 5 | 10 |
| 87 | α-tocoperol | — | 75 | 31 |
| 88 | —CO—O—CH$_3$ | — | 15 | 32 |
| 89 | —CO—O—n-heptyl | — | 62 | 30 |
| 90 | —COOH | — | 18 | 59 |
| 91 | ascorbyl palmitate | — | 22 | 20 |
| According to the invention | | | | |
| 92 | —CO—O—n-dodecyl | 1 | 105 | 35 |
| 93 | —CO—O—n-tetradecyl | 3 | 104 | 37 |
| 94 | —CO—O—3,7,11,15-tetramethylhexadecyl | 8 | 87 | 34 |
| 95 | —CO—O—n-eicosyl | 6 | 86 | 35 |
| 96 | —CH$_2$—O—CO—n-heptadecyl | 22 | 106 | 45 |
| 97 | —CH$_2$—CH$_2$—O—CO—n-heptadecyl | 15 | 77 | 52 |
| 98 | —CH$_2$—CH$_2$—O—CO—O—n-hexadecyl | 24 | 97 | 47 |
| 99 | —CO—NH—n-dodecyl | — | 80 | 40 |

$^{(x)}$cf. footnote to Table 4

We claim:

1. A chroman derivative of the formula I

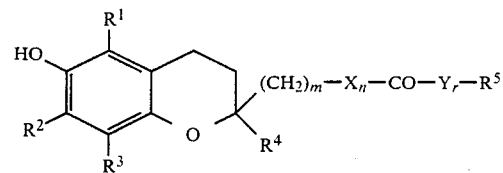

where R$^1$, R$^2$, R$^3$ and R$^4$ are each H or C$_1$-C$_4$-alkyl, R$^5$ is C$_{10}$-C$_{30}$-alkyl or C$_{10}$-C$_{30}$-alkenyl, X and Y are each O, NH or S, m is 0, 1, 2 or 3 and n and r are each 0 or 1.

2. A chroman derivative as set forth in claim 1, where R$^1$, R$^2$, R$^3$ and R$^4$ are each methyl and X and/or Y is oxygen.

3. A stabilized composition of matter comprising polypropylene and, as a stabilizer, from 0.01 to 20% by weight of a chroman derivative I as set forth in claim 1.

4. A stabilized composition as set forth in claim 3, wherein the composition further contains from 50 to 500% by weight, based on the weight of stabilizer I, of a stabilizer-synergist.

* * * * *